US011521740B2

(12) United States Patent
Abrami et al.

(10) Patent No.: US 11,521,740 B2
(45) Date of Patent: Dec. 6, 2022

(54) NATURAL LANGUAGE PROCESSING OF A MOTION ALPHABET FOR UNSUPERVISED CLINICAL SCORING

(71) Applicant: International Business Machines Corporation, Armonk, NY (US)

(72) Inventors: Avner Abrami, New York, NY (US); Vittorio Caggiano, New York, NY (US); John Jeremy Rice, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/001,063

(22) Filed: Jun. 6, 2018

(65) Prior Publication Data
US 2019/0378616 A1    Dec. 12, 2019

(51) Int. Cl.
*G16H 50/20* (2018.01)
*G06N 7/00* (2006.01)
*G06F 40/20* (2020.01)

(52) U.S. Cl.
CPC ............ *G16H 50/20* (2018.01); *G06F 40/20* (2020.01); *G06N 7/00* (2013.01)

(58) Field of Classification Search
None
See application file for complete search history.

(56) References Cited

U.S. PATENT DOCUMENTS

| 6,967,652 | B1 * | 11/2005 | Nubling | A61B 5/339 345/440 |
| 8,187,209 | B1 | 5/2012 | Giuffrida | |
| 8,732,096 | B1 * | 5/2014 | Glukhov | G16H 50/20 706/12 |
| 9,445,769 | B2 | 9/2016 | Ghassemzadeh et al. | |
| 9,687,180 | B1 | 6/2017 | Deninger et al. | |
| 2005/0234309 | A1 | 10/2005 | Klapper | |
| 2007/0172803 | A1 * | 7/2007 | Hannaford | G16H 40/20 434/262 |
| 2009/0048542 | A1 | 2/2009 | Varadan et al. | |
| 2009/0327171 | A1 | 12/2009 | Tan et al. | |

(Continued)

FOREIGN PATENT DOCUMENTS

WO    2017210729 A1    12/2017

OTHER PUBLICATIONS

Ghasemzadeh et al., "Coordination Analysis of Human Movements With Body Sensor Networks: A Signal Processing Model to Evaluate Baseball Swings," Mar. 2011, IEEE Sensors Journal, vol. 11, No. 3, pp. 603-610. (Year: 2011).*

(Continued)

*Primary Examiner* — Jonathon A. Szumny
(74) *Attorney, Agent, or Firm* — Amin, Turocy & Watson, LLP

(57) ABSTRACT

Techniques that facilitate natural language processing of a motion alphabet for unsupervised clinical scoring are described. In one example, a system converts sensor data from one or more movement capturing devices associated with a user identity into symbolic data indicative of a symbolic representation of the sensor data. The system also analyzes the symbolic data associated with the one or more movement capturing devices based on a symbolic analysis technique.

16 Claims, 11 Drawing Sheets

(56) References Cited

U.S. PATENT DOCUMENTS

| | | |
|---|---|---|
| 2010/0030119 A1 | 2/2010 | McNames et al. |
| 2010/0169409 A1 | 7/2010 | Fallon et al. |
| 2011/0092860 A1 | 4/2011 | Salarian et al. |
| 2012/0323521 A1 | 12/2012 | De Foras et al. |
| 2013/0028489 A1 | 1/2013 | Tracton et al. |
| 2013/0185231 A1* | 7/2013 | Baras .................. G16H 50/20 706/12 |
| 2014/0168246 A1* | 6/2014 | Tzao ...................... A61B 5/00 345/581 |
| 2014/0257141 A1 | 9/2014 | Giuffrida et al. |
| 2015/0066538 A1* | 3/2015 | Dantsker ............. G06F 19/3418 705/3 |
| 2015/0073310 A1 | 3/2015 | Pracar et al. |
| 2015/0370333 A1 | 12/2015 | Ataee et al. |
| 2016/0110584 A1* | 4/2016 | Remiszewski ........ G06T 7/0014 382/133 |
| 2017/0000387 A1 | 1/2017 | Forth et al. |
| 2017/0113045 A1* | 4/2017 | Baldassano ........ A61N 1/36064 |
| 2018/0092572 A1* | 4/2018 | Sanchez ................ G16H 50/70 |
| 2018/0204111 A1* | 7/2018 | Zadeh ................. G06N 3/0436 |
| 2019/0000350 A1* | 1/2019 | Narayan .............. A61B 5/4818 |
| 2019/0046039 A1* | 2/2019 | Ramesh ............... A61B 5/0024 |
| 2019/0370632 A1* | 12/2019 | Hashemi ................ G06N 3/084 |

OTHER PUBLICATIONS

Ghassemzadeh et al., "A Motion Sequence Fusion Technique Based on PCA for Activity Analysis in Body Sensor Networks," Sep. 2009, 31st Annual Conference of the IEEE EMBS, pp. 3146-3149. (Year: 2009).*

Anna et al., "Developing a Motion Language: Gait Analysis from Accelerometer Sensor Systems," 2009, Pervasive Health. (Year: 2009).*

Ghasemzadeh et al., "A Phonological Expression for Physical Movement Monitoring in Body Sensor Networks," 2008, IEEE, pp. 58-68. (Year: 2008).*

Banos et al., "PhysioDroid: Combining Wearable Health Sensors and Mobile Devices for Ubiquitous, Continuous, and Personal Monitoring," 2014, The Scientific World Journal, vol. 2014, Article ID 490824, pp. 1-11. (Year: 2014).*

Patel et al., "Home Monitoring of Patients with Parkinson's Disease via Wearable Technology and a Web-based Application," Aug. 2010, Annual Conference of the IEEE Engineering in Medicine and Biology Society. (Year: 2010).*

Anna et al., "A Symbol-Based Approach to Gait Analysis From Acceleration Signals: Identification and Detection of Gait Events and a New Measure of Gait Symmetry," Sep. 2010, IEEE Transactions on Information Technology in Biomedicine, vol. 14, No. 5, pp. 1180-1187. (Year: 2010).*

Schlachetzki et al., "Wearable sensors objectively measure gait parameters in Parkinson's disease," Oct. 2017, PLoS One, pp. 1-18. (Year: 2017).*

Wang, "Machine Learning for Gait Classification," 2017 (Year: 2017).*

Li et al., "A Data-Driven Predictive Approach for Drug Delivery Using Machine Learning Techniques," PLoS One 7(2) (Year: 2012).*

Pasluosta, et al., "An Emerging Era in the Management of Parkinson's Disease: Wearable Technologies and the Internet of Things," DOI 10.1109/JBHI.2015.2461555, IEEE Journal of Biomedical and Health Informatics, 2015, 10 pages.

* cited by examiner

NATURAL LANGUAGE PROCESSING OF A MOTION ALPHABET FOR UNSUPERVISED CLINICAL SCORING

BACKGROUND

The subject disclosure relates generally to wearable device systems, and more specifically, to analysis of sensor data generated by wearable devices.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate natural language processing of a motion alphabet for unsupervised clinical scoring are described.

According to an embodiment, a system can comprise a measurement component and an analysis component. The measurement component can convert sensor data from one or more movement capturing devices associated with a user identity into symbolic data indicative of a symbolic representation of the sensor data. The analysis component can analyze the symbolic data associated with the one or more movement capturing devices based on a symbolic analysis technique. In an embodiment, the analysis component can analyze the symbolic data associated with the one or more movement capturing devices based on a natural language processing technique. In certain embodiments, the analysis component can determine whether the sensor data satisfies a defined criterion associated with a medical condition based on a distance measurement between two or more output values of a natural language processing model associated with the symbolic data.

According to another embodiment, a computer-implemented method is provided. The computer-implemented method can comprise converting, by a system operatively coupled to a processor, sensor data from one or more sensors associated with a user identity into symbolic data indicative of a symbolic representation of the sensor data. The computer-implemented method can also comprise analyzing, by the system, the symbolic data associated with the one or more sensors based on a natural language processing technique. In certain embodiments, the computer-implemented method can additionally comprise determining, by the system, whether the sensor data satisfies a defined criterion associated with a medical condition based on the analyzing the symbolic data associated with the natural language processing technique.

According to yet another embodiment, a computer program product for facilitating natural language processing of a motion alphabet for unsupervised clinical scoring can comprise a computer readable storage medium having program instructions embodied therewith. The program instructions can be executable by a processor and cause the processor to convert, by the processor, sensor data from one or more sensors associated with a user identity into symbolic data indicative of a symbolic representation of the sensor data. The program instructions can also cause the processor to analyze, by the processor, the symbolic data associated with the one or more sensors based on a natural language processing technique. Furthermore, the program instructions can cause the processor to determine, by the processor, whether the sensor data satisfies a defined criterion associated with a medical condition based on analysis of the symbolic data associated with the natural language processing technique.

DETAILED DESCRIPTION

Figure 1:
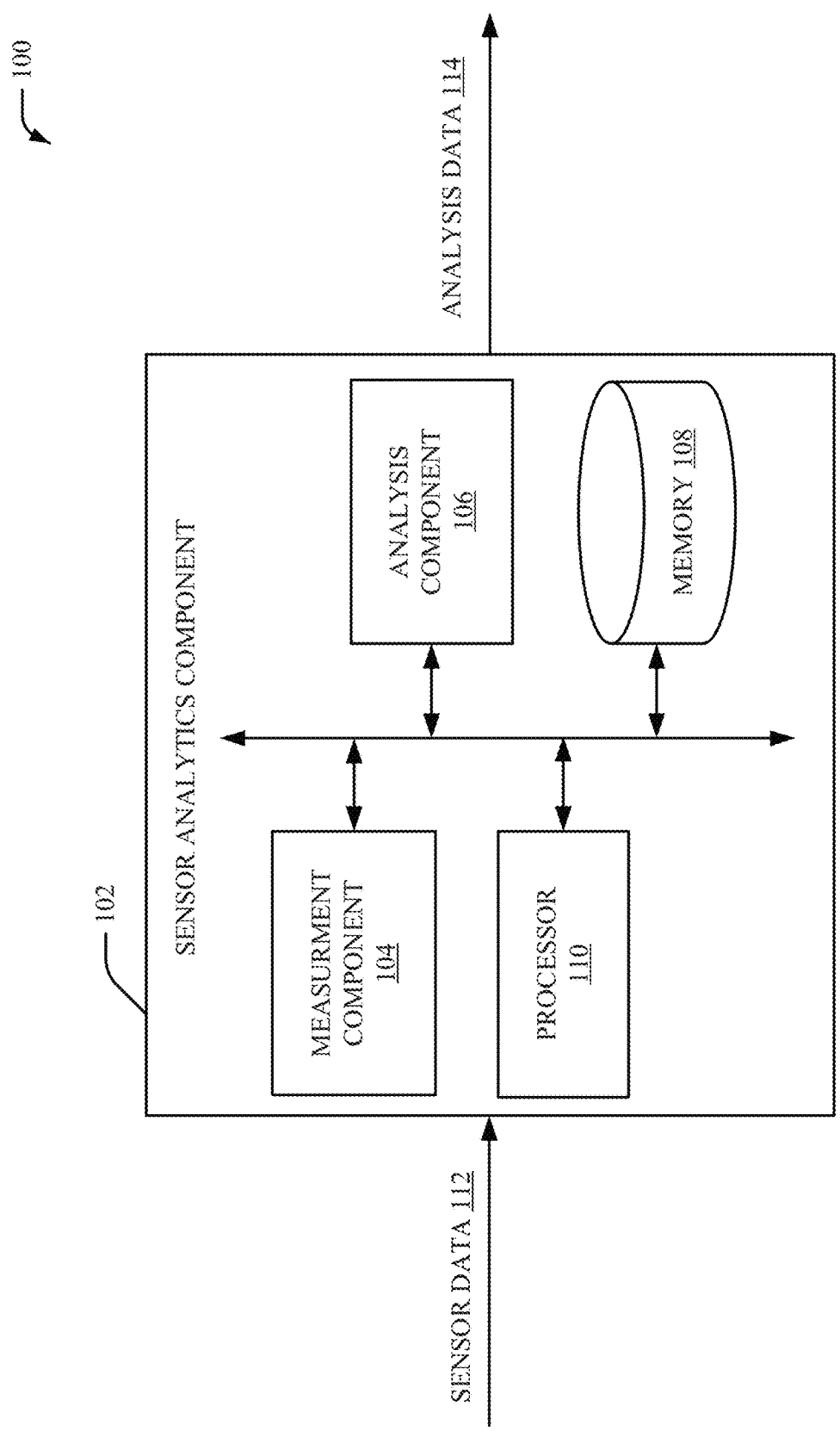
FIG. 1 illustrates a block diagram of an example, non-limiting system that includes a sensor analytics component in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Wearable technology can be related to electronic devices with sensors and/or microcontrollers than can be worn on a human body. For example, a wearable device can be utilized to collect data regarding health of a user such as heart rate, blood pressure, movement patterns, etc. However, analyzing data collected by a wearable device is difficult. For instance, it is difficult to make medical decisions regarding a user that employs a wearable device based on data collected by the wearable device.

To address these and/or other issues, embodiments described herein include systems, computer-implemented methods, and computer program products that facilitate natural language processing of a motion alphabet for unsupervised clinical scoring. For instance, data collected by one or more sensors can be converted into a motion alphabet. The data collected by the one or more sensors can be, for example, multi-dimensional continuous sensor data. The motion alphabet can be a symbolic representation of the data collected by the one or more sensors. For example, the motion alphabet (e.g., the symbolic representation of the data collected by the one or more sensors) can be a set of symbols that are a discrete and/or a compact representation of high-dimensional continuous information. Furthermore, the motion alphabet can be analyzed using natural language processing to provide, for example, unsupervised clinical scoring associated with a user. In an embodiment, the data collected by the one or more sensors can be transformed into a symbolic representation and the symbolic representation can be modeled using one or more natural language processing techniques. In one example, the symbolic representation can be modeled as a Markov-Chain. However, it is to be appreciated that the symbolic representation can be modeled using different natural language processing. In an aspect, the symbolic representation can be a compressed version of the data collected by the one or more sensors. In certain embodiments, unsupervised detection of a transition between states associated with data collected by the one or more sensors can be performed. A transition can be, for example, a transition between a healthy condition and a disease condition for a user associated with the one or more sensors, a transition between a state under influence of medication (e.g., an "on" state) and when the medication wears off (e.g., an "off" state) associated with the data collected by the one or more sensors, etc. In an aspect, a transition between states can be determined based on a changing distance between derived distributions of symbol sequences associated with the motion alphabet. For example, a transition between states can be determined based on a changing distance between stationary distributions for a Markov-Chain associated with the motion alphabet. As such, unsupervised description of a user status (e.g., a patient status) associated with one or more sensors can be provided without labeled or constrained actions. Additionally, recognition of a data state for data collected by one or more sensors (e.g., recognition of a motor state of a patient related to data collected by one or more sensors) can be improved. Moreover, processing of data collected by one or more sensors can be improved. For instance, quality of analysis of data collected by one or more sensors can be improved. Furthermore, difficulty of analyzing data collected by one or more sensors can be reduced. Storage requirements for data collected by one or more sensors can be reduced and/or a data rate for transmitting data collected by one or more sensors can be improved.

FIG. 1 illustrates a block diagram of an example, non-limiting system 100 that facilitates natural language processing of a motion alphabet for unsupervised clinical scoring in accordance with one or more embodiments described herein. In various embodiments, the system 100 can be a condition detection system associated with technologies such as, but not limited to, sensor technologies, medical device technologies, healthcare technologies, health monitoring technologies, wearable device technologies, wearable heath device technologies, movement capturing device technologies, pharmaceutical technologies, machine learning technologies, artificial intelligence technologies, digital technologies, data analysis technologies, data analytics technologies, cloud computing technologies, computer technologies, server technologies, and/or other technologies. The system 100 can employ hardware and/or software to solve problems that are highly technical in nature, that are not abstract and that cannot be performed as a set of mental acts by a human. Further, some of the processes performed may be performed by one or more specialized computers (e.g., one or more specialized processing units, a specialized computer with a sensor analytics component, etc.) for carrying out defined tasks related to sensor analytics and/or data monitoring. The system 100 and/or components of the system can be employed to solve new problems that arise through advancements in technologies mentioned above and/or computer architecture, and the like. One or more embodiments of the system 100 can provide technical improvements to a system associated with technologies such as, but not limited to, sensor systems, medical device systems, healthcare systems, health monitoring systems, wearable device systems, wearable heath device systems, movement capturing device systems, pharmaceutical systems, machine learning systems, artificial intelligence systems, digital systems, data analysis systems, data analytics systems, cloud computing systems, computer systems, server systems, and/or other systems.

In the embodiment shown in FIG. 1, the system 100 can include a sensor analytics component 102. As shown in FIG. 1, the sensor analytics component 102 can include a measurement component 104 and an analysis component 106. Aspects of the sensor analytics component 102 can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. In an aspect, the sensor analytics component 102 can also include memory 108 that stores computer executable components and instructions. Furthermore, the sensor analytics component 102 can include a processor 110 to facilitate execution of the instructions (e.g., computer executable components and corresponding instructions) by the sensor analytics component 102. As shown, the measurement component 104, the analysis component 106, the memory 108 and/or the processor 110 can be electrically and/or communicatively coupled to one another in one or more embodiments. In certain embodiments, the sensor analytics component 102 can be in communication with a wearable device system and/or a cloud computing system.

The sensor analytics component 102 (e.g., the measurement component 104 of the sensor analytics component 102) can receive sensor data 112. The sensor data 112 can be sensor data received from one or more sensors. In an aspect, the sensor data 112 can be associated with a user (e.g., a user identity). For instance, the sensor data 112 can be associated with a patient (e.g., a patient body). The one or more sensors can be one or more sensors of one or more sensor devices associated with the user (e.g., the user identity). For example, the one or more sensors can be one or more sensors of one or more movement capturing devices associated with the user (e.g., the user identity). Additionally or alternatively, the one or more sensors can be one or more sensors of one or more wearable devices associated with the user (e.g., the user identity). Additionally or alternatively, the one or more sensors can be one or more sensors of one or more medical wearable devices associated with the user (e.g., the user identity). Additionally or alternatively, the one or more sensors can be one or more sensors of one or more smart devices associated with the user (e.g., the user identity). However, it is to be appreciated that the one or more sensors can additionally or alternatively be one or more sensors of one or more different sensor devices associated with the user (e.g., the user identity). In certain embodiments, the sensor data 112 can additionally or alternatively be captured by one or more cameras and/or one or more other motion capture systems. In one example, the sensor data 112 can be captured with markers. In another example, the sensor data 112 can be captured with without markers. In an aspect, the one or more sensors can be worn by the user (e.g., the user identity). For example, the one or more sensors can be worn on the patient (e.g., worn on the patient body). In an embodiment, the one or more sensors can be one or more wrist reference sensors. For example, the one or more sensors can be one or more accelerometers, one or more gyroscopes and/or one or more other movement capturing devices associated with a wrist reference device. In one example, the one or more wrist reference sensors can be implemented on a smart watch. Additionally or alternatively, the one or more sensors can be one or more lumbar reference sensors. For example, the one or more sensors can be one or more accelerometers, one or more gyroscopes and/or one or more other movement capturing devices associated with a lumbar reference device. Additionally or alternatively, the one or more sensors can be one or more wearable sensors. For example, the one or more sensors can be one or more accelerometers, one or more gyroscopes, one or more magnometers and/or one or more other movement capturing devices associated with a wearable device. In certain embodiments, the one or more sensors can additionally or alternatively be one or more biosensors that capture bio-activity associated with the user (e.g., the user identity). For example, the one or more sensors can be one or more electrocardiography sensors that obtain electrical activity of a biological heart of the patient during a certain time period. In certain embodiments, the one or more sensors can additionally or alternatively be one or more auxiliary sensors located in one or objects and/or one or more devices auxiliary to the user (e.g., the user identity).

The measurement component 104 can convert the sensor data 112 into symbolic data indicative of a symbolic representation of the sensor data 112. For example, the symbolic data can be representative of a motion alphabet related to the sensor data 112. In an aspect, the symbolic data can be a discrete representation of the sensor data 112 that can be categorized into one or more classifications. For instance, the symbolic data can be a sequence of discrete symbols where a symbol is an identifier for a portion of the sensor data 112. In one example, the symbolic data can be a set of alphabetical letters associated with different portions of the sensor data 112. In another aspect, the symbolic data can be a compressed version of the sensor data 112. In an embodiment, the measurement component 104 can capture a set of data windows associated with the sensor data 112 to facilitate conversion of the sensor data 112 into the symbolic data. For instance, the measurement component 104 can segment the sensor data 112 into a set of data windows associated with a defined interval of time. In one example, the set of data windows can be a set of overlapping data windows. Furthermore, the measurement component 104 can assign a set of symbols to the set of data windows. For example, the measurement component 104 can assign a first symbol to a first data window from the set of data windows, the measurement component 104 can assign a second symbol to a second data window from the set of data windows, the measurement component 104 can assign a third symbol to a third data window from the set of data windows, etc. In an embodiment, the measurement component 104 can store the symbolic data in memory (e.g., the memory 108 or a different memory). In another embodiment, the measurement component 104 can transmit the symbolic data to, for example, the analysis component 106 and/or another component.

The analysis component 106 can analyze the symbolic data based on a symbolic analysis technique. For instance, the symbolic analysis technique can determine one more interpretations for the sensor data 112 based on the symbolic data. In an embodiment, the analysis component 106 can analyze the symbolic data based on a natural language processing technique. For example, the analysis component 106 can determine syntax, semantics and/or discourse associated with the symbolic data using a natural language processing technique. The natural language processing technique can be an artificial intelligence technique that processes the symbolic data to learn and/or derive meaning from the symbolic data. In an aspect, the natural language processing technique can, for example, compute a characteristic distribution of the symbolic data that defines a probability distribution of the symbolic data. In another aspect, the natural language processing technique can generate a natural language processing model of the symbolic data. In an embodiment, the analysis component 106 can analyze the symbolic data based on a Markov-Chain technique. The Markov-Chain technique can generate a Markov chain for the symbolic data. The Markov chain can include a set of states associated with the symbolic data. Furthermore, the Markov chain can include a set of transitions between the set of states associated with the Markov chain. In an aspect, the Markov-Chain technique can, for example, compute a stationary distribution from the set of transitions associated with the Markov chain that defines a probability distribution of the symbolic data that can remain unchanged in the Markov chain during an interval of time. However, it is to be appreciated that the analysis component 106 can analyze the symbolic data based on a different type of natural language processing technique. Additionally or alternatively, in certain embodiments, the analysis component 106 can analyze the symbolic data based on a non-natural language processing associated with symbolic analysis. In an embodiment, the analysis component 106 can generate analysis data 114. The analysis data 114 can include syntax data, semantics data and/or discourse data associated with the symbolic data. For example, the analysis data 114 can include information associated with the natural language processing technique (e.g., the Markov-Chain technique). In an aspect, the analysis data 114 can provide clinical scoring associated with the sensor data 112 and/or the symbolic data. For example, the analysis data 114 can provide motion behavior scoring associated with the user (e.g., the user identity) related to the sensor data 112. For instance, the analysis data 114 can determine a motor state for the user (e.g., the user identity) related to the sensor data 112. In another example, the analysis data 114 can indicate a whether the sensor data 112 is associated with a medical condition (e.g., healthy vs. disease, etc.). In yet another example, the analysis data 114 can indicate a whether the sensor data 112 is associated with a binary logic criterion (e.g., on vs. off, etc.). In a non-limiting example, the analysis data 114 can provide analysis regarding an effect of a medication for the user (e.g., the user identity) related to the sensor data 112. In another non-limiting example, the analysis data 114 can provide analysis regarding severity of a medical condition for the user (e.g., the user identity) related to the sensor data 112. A medical condition can be, for example, a motor-based impairment, a neurological condition, and/or another type of medical condition.

In certain embodiments, the analysis component 106 can employ machine learning and/or principles of artificial intelligence (e.g., a machine learning process) associated with natural language processing to analyze the symbolic data. For example, the analysis component 106 can employ machine learning and/or principles of artificial intelligence (e.g., a machine learning process) associated with natural language processing to learn one or more patterns, one or more inferences, one or more correlations, one or more features and/or information related to the symbolic data. In an aspect, the analysis component 106 can employ machine learning and/or principles of artificial intelligence (e.g., a machine learning process) associated with natural language processing to generate the analysis data 114. The analysis component 106 can perform learning with respect to learning one or more patterns, one or more inferences, one or more correlations, one or more features and/or information related to the symbolic data explicitly or implicitly. In an aspect, the analysis component 106 can learn one or more patterns, one or more inferences, one or more correlations, one or more features and/or information related to the symbolic data based on classifications, correlations, inferences and/or expressions associated with principles of artificial intelligence. For instance, the analysis component 106 can employ an automatic classification system and/or an automatic classification process to learn one or more patterns, one or more inferences, one or more correlations, one or more features and/or information related to the symbolic data. In one example, the analysis component 106 can employ a probabilistic and/or statistical-based analysis (e.g., factoring into the analysis utilities and costs) to learn and/or generate inferences with respect to the symbolic data. In an aspect, the analysis component 106 can include an inference component (not shown) that can further enhance automated aspects of the analysis component 106 utilizing in part inference based schemes to learn one or more patterns, one or more inferences, one or more correlations, one or more features and/or information related to the symbolic data.

The analysis component 106 can employ any suitable machine-learning based techniques, statistical-based techniques and/or probabilistic-based techniques. For example, the analysis component 106 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the analysis component 106 can perform a set of machine learning computations associated with learning one or more patterns, one or more inferences, one or more correlations, one or more features and/or information related to the symbolic data. For example, the analysis component 106 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations to learn one or more patterns, one or more inferences, one or more correlations, one or more features and/or information related to the symbolic data.

In an embodiment, the analysis component 106 can integrate the symbolic data into a machine learning model. The machine learning model can be, for example, a natural language processing model. In an embodiment, the machine learning model can be included in the analysis data 114. In an aspect, the machine learning model generated by the analysis component 106 can determine whether a classifiable pattern is associated with the symbolic data to determine whether the sensor data 112 is associated with a medical condition. In one example, the machine learning model can be a classifier that provides a confidence score related to a medical condition for the user associated with the sensor data 112. In certain embodiments, the analysis component 106 can determine a distance between a medical condition associated with a user (e.g., a user identity) related to the sensor data 112 and a normal condition. For example, the analysis component 106 can employ results of the natural language processing technique (e.g., the Markov-Chain technique) associated with the symbolic data to facilitate determination of a distance between a normal condition and a medical condition associated with a user (e.g., a user identity) related to the sensor data 112. In one example, the analysis component 106 can determine whether the sensor data 112 satisfies a defined criterion associated with a medical condition based on a distance measurement (e.g., a similarity measure) between two or more output values of the machine learning model associated with the symbolic data. However, it is to be appreciated that the machine learning model can be associated with another type of machine learning technique and/or another type of artificial intelligence technique.

It is to be appreciated that the sensor analytics component 102 (e.g., the measurement component 104 and/or analysis component 106) performs a sensor analytics process that cannot be performed by a human (e.g., is greater than the capability of a single human mind). For example, an amount of data processed, a speed of processing of data (e.g., a speed of processing data associated with multiple parties) and/or data types processed by the sensor analytics component 102 (e.g., the measurement component 104 and/or analysis component 106) over a certain period of time can be greater, faster and different than an amount, speed and data type that can be processed by a single human mind over the same period of time. The sensor analytics component 102 (e.g., the measurement component 104 and/or analysis component 106) can also be fully operational towards performing one or more other functions (e.g., fully powered on, fully executed, etc.) while also performing the above-referenced condition sensor analytics process. Moreover, the sensor analytics component 102 (e.g., the measurement component 104 and/or analysis component 106) can determine information that is impossible to obtain manually by a user. For example, a type of information included in the analysis data 114, timing for generating the analysis data 114, an amount of information included in the analysis data 114 and/or a variety of information included in the analysis data 114 can be more complex than information obtained manually by a user.

Figure 2:
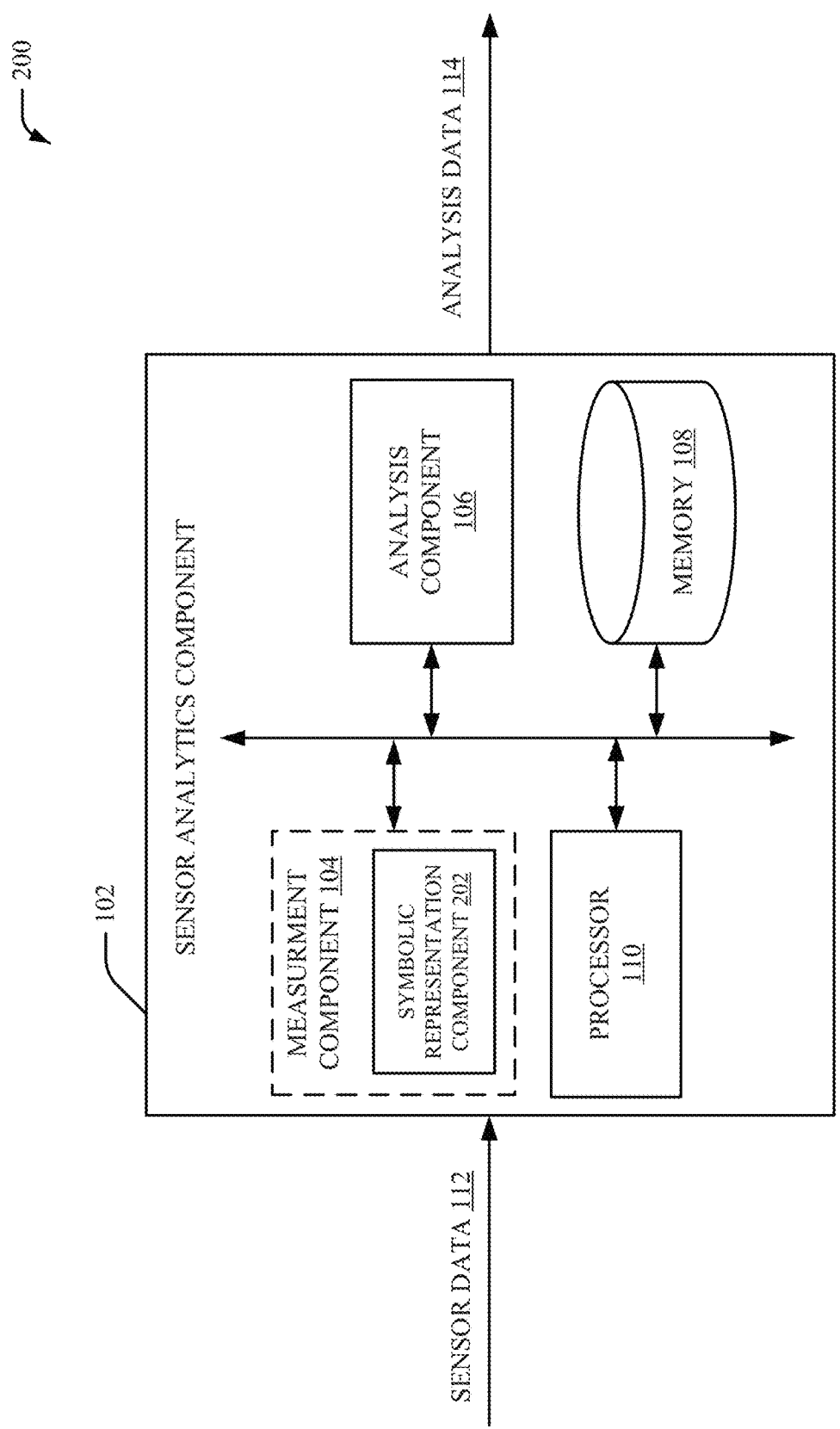
FIG. 2 illustrates a block diagram of another example, non-limiting system that includes a sensor analytics component in accordance with one or more embodiments described herein.

FIG. 2 illustrates a block diagram of an example, non-limiting system 200 in accordance with one or more embodiments described herein. Repetitive description of like elements employed in other embodiments described herein is omitted for sake of brevity.

The system 200 includes the sensor analytics component 102. The sensor analytics component 102 can include the measurement component 104, the analysis component 106, the memory 108 and/or the processor 110. In the embodiment shown in FIG. 2, the measurement component 104 can include a symbolic representation component 202. The symbolic representation component 202 can convert the sensor data 112 into the symbolic data indicative of the symbolic representation of the sensor data 112. In an embodiment, the symbolic representation component 202 can convert the sensor data 112 into the symbolic data based on a clustering technique that groups and/or classifies the sensor data 112. For example, the symbolic representation component 202 can tokenize data windows associated with the sensor data 112 to facilitate generation of the symbolic data. In a non-limiting example, the symbolic representation component 202 can employ a K-means clustering technique associated with vector quantization of the sensor data 112. However, it is to be appreciated that the symbolic representation component 202 can employ a different type of clustering technique. In an aspect, the symbolic representation component 202 can assign a symbol to a data window associated with the sensor data 112 to facilitate generation of the symbolic data. For instance, the symbolic representation component 202 can assign a first symbol to a first data window associated with the sensor data 112, the symbolic representation component 202 can assign a second symbol to a second data window associated with the sensor data 112, the symbolic representation component 202 can assign a third symbol to a third data window associated with the sensor data 112, etc. to generate a sequence of discrete symbols associated with the symbolic data. In an aspect, a set of symbols associated with the symbolic data can be formatted for natural language processing. For example, a set of symbols associated with the symbolic data can be associated with a natural language processing domain. In certain embodiments, the symbolic representation component 202 can convert the sensor data 112 into the symbolic data to facilitate compression of the sensor data 112 for storage and/or transmission.

Figure 3:
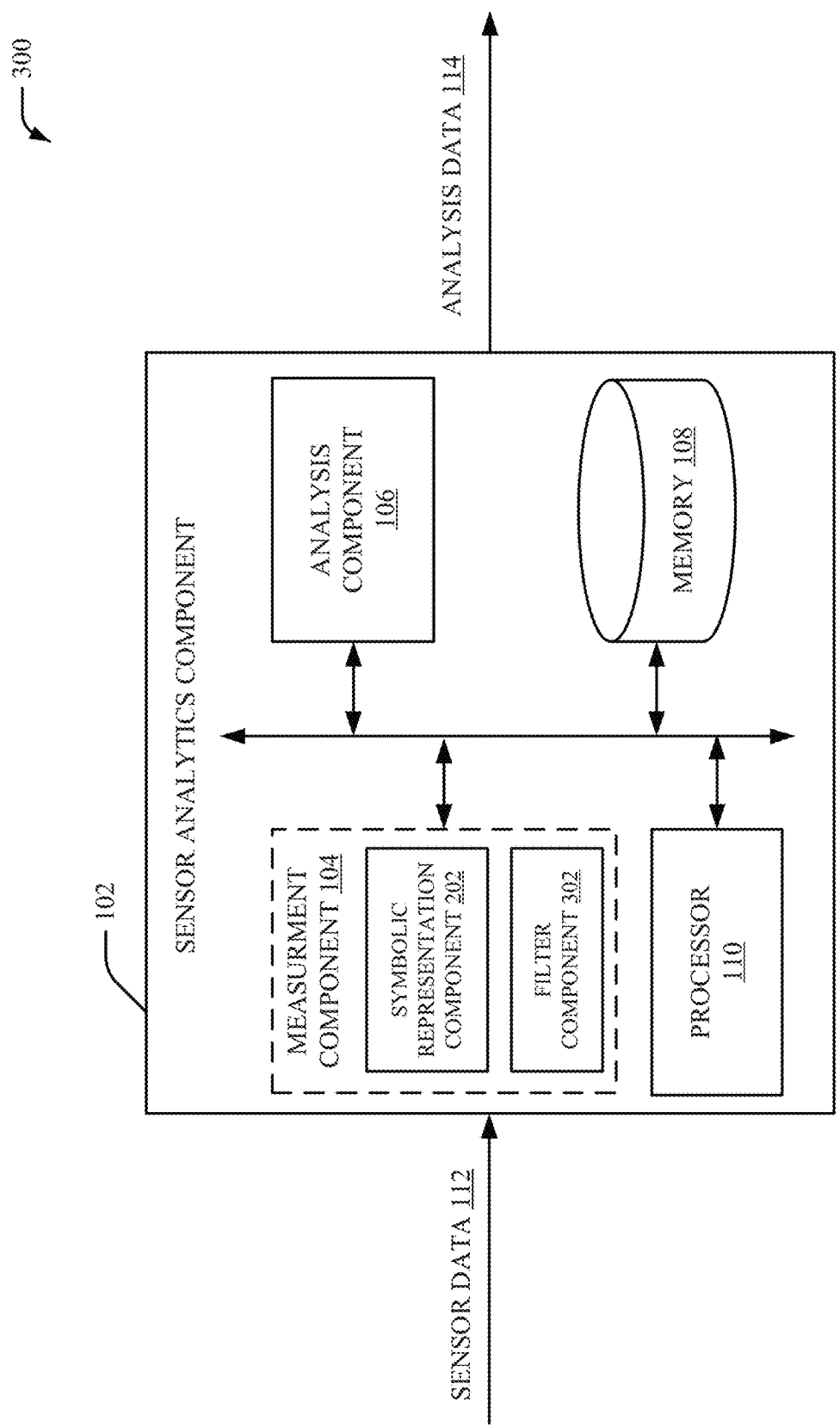
FIG. 3 illustrates a block diagram of yet another example, non-limiting system that includes a sensor analytics component in accordance with one or more embodiments described herein.

FIG. 3 illustrates a block diagram of an example, non-limiting system 300 in accordance with one or more embodiments described herein. Repetitive description of like elements employed in other embodiments described herein is omitted for sake of brevity.

The system 300 includes the sensor analytics component 102. The sensor analytics component 102 can include the measurement component 104, the analysis component 106, the memory 108 and/or the processor 110. In the embodiment shown in FIG. 3, the measurement component 104 can include the symbolic representation component 202 and/or a filter component 302. The filter component 302 can filter the sensor data 112. In an embodiment, the filter component 302 can filter the sensor data 112 prior to being transformed into the symbolic data. For example, the filter component 302 can perform preprocessing associated with the sensor data 112. In an aspect, the filter component 302 can filter noise from the sensor data 112. Additionally or alternatively, the filter component 302 can filter a set of frequency ranges (e.g., a set of unwanted frequency ranges) from the sensor data 112. In an example, the set of frequency ranges can be associated with a continuous bias and/or high frequency. In an embodiment, the filter component 302 can filter the sensor data 112 to facilitate monitoring of a set of signals in a range of movement behaviors of interest for a user associated with the sensor data 112. For instance, the filter component 302 can filter the sensor data 112 based on filter data indicative of information for a range of movement associated with a user. In one example, the filter data can include a set of frequency ranges and/or a set of parameters associated with a range of movement of a user. However, it is to be appreciated that the filter component 302 can filter the sensor data 112 via another type of filtering technique.

Figure 4:
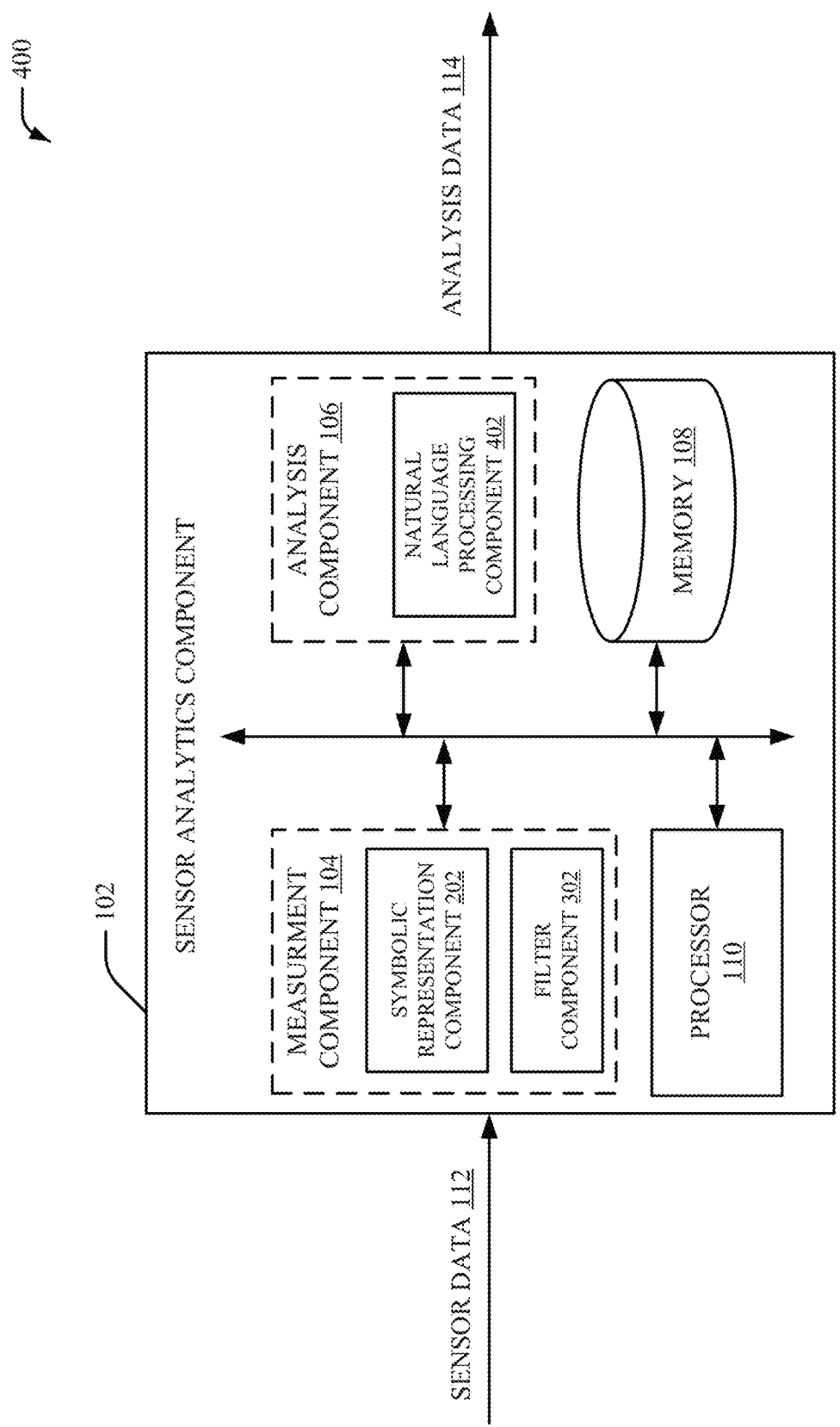
FIG. 4 illustrates a block diagram of yet another example, non-limiting system that includes a sensor analytics component in accordance with one or more embodiments described herein.

FIG. 4 illustrates a block diagram of an example, non-limiting system 400 in accordance with one or more embodiments described herein. Repetitive description of like elements employed in other embodiments described herein is omitted for sake of brevity.

The system 400 includes the sensor analytics component 102. The sensor analytics component 102 can include the measurement component 104, the analysis component 106, the memory 108 and/or the processor 110. In the embodiment shown in FIG. 4, the measurement component 104 can include the symbolic representation component 202 and/or the filter component 302. Furthermore, the analysis component 106 can include a natural language processing component 402. The natural language processing component 402 can model the symbolic data using one or more natural language processing techniques. In an embodiment, the natural language processing component 402 can model the symbolic data using a Markov-Chain technique. The Markov-Chain technique can generate a Markov chain for the symbolic data. The Markov chain can include a set of states associated with the symbolic data. Furthermore, the Markov chain can include a set of transitions between the set of states associated with the Markov chain. In an aspect, a symbol associated with the symbolic data can correspond to a state of a Markov-Chain. Furthermore, a transition matrix associated with the Markov-Chain can be computed by analyzing a transition between symbols (e.g., between states of the Markov-Chain). In another aspect, an amount of time that the Markov-Chain processing a symbol associated with the symbolic data can correspond to a stationary distribution of the symbolic data. However, it is to be appreciated that the natural language processing component 402 can additionally or alternatively model the symbolic data using one or more different natural language processing techniques.

Figure 5:
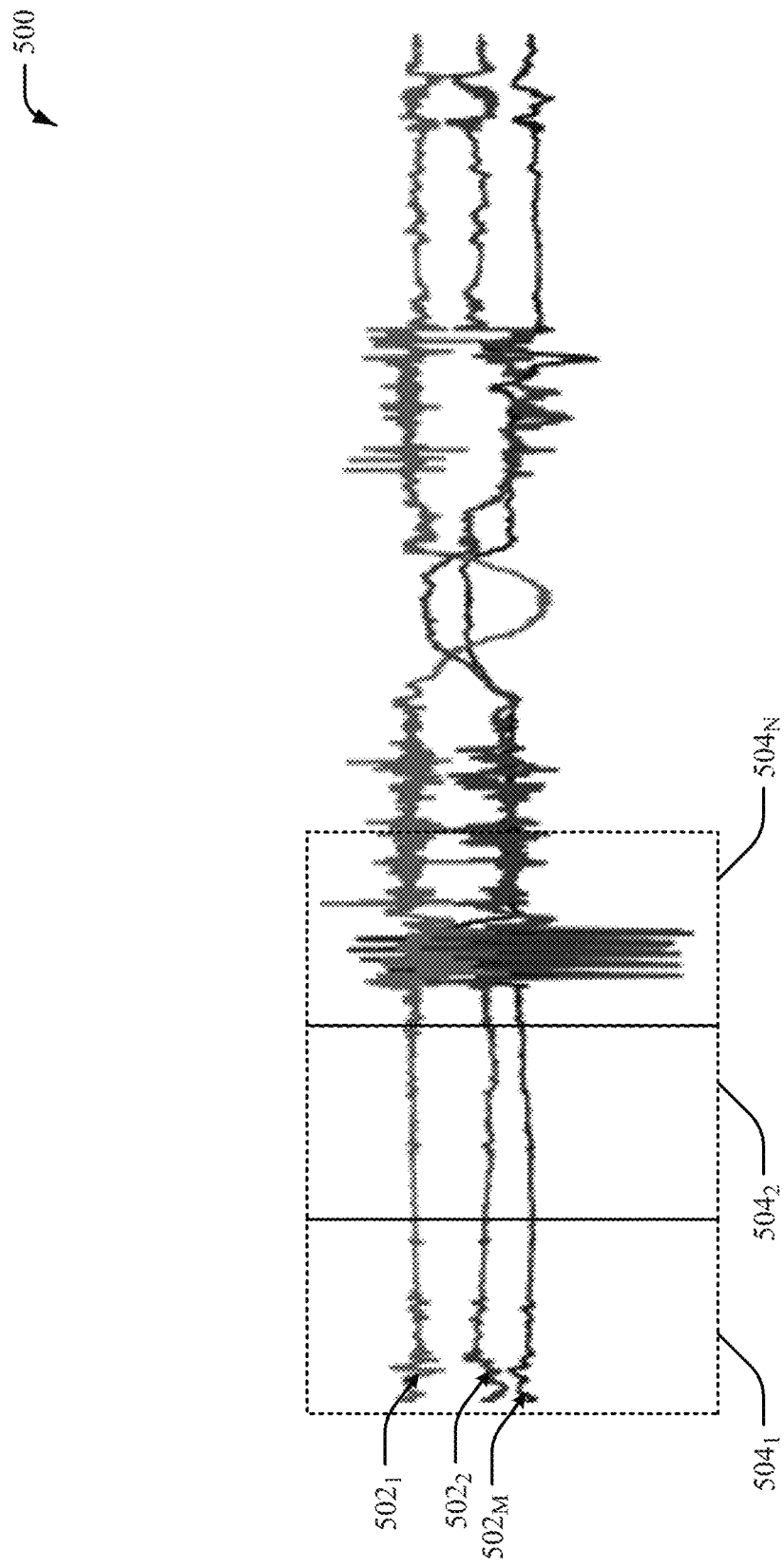
FIG. 5 illustrates an example, non-limiting system that includes sensor data and data windows in accordance with one or more embodiments described herein.

FIG. 5 illustrates an example, non-limiting system 500 in accordance with one or more embodiments described herein. Repetitive description of like elements employed in other embodiments described herein is omitted for sake of brevity.

The system 500 includes sensor data $502_{1-M}$, where M is an integer. For example, sensor data $502_1$ can be sensor data from a first sensor, sensor data $502_2$ can be sensor data from a second sensor, sensor data $502_M$ can be sensor data from an Mth sensor, etc. In an aspect, the sensor data $502_{1-M}$ can correspond to the sensor data 112 provided to the sensor analytics component 102. The system 500 also includes data windows $504_{1-N}$, where N is an integer. For example, data window $504_1$ can be a first data window associated with the sensor data $502_{1-M}$, data window $504_2$ can be a second data window associated with the sensor data $502_{1-M}$, data window $504_N$ can be an Nth data window associated with the sensor data $502_{1-M}$, etc. In an aspect, the data windows $504_{1-M}$ can store the sensor data $502_{1-M}$ as a set of one-dimensional data vectors. For example, the data window $504_1$ can store a first portion of the sensor data $502_{1-M}$ in a first one-dimensional data vector, the data window $504_2$ can store a second portion of the sensor data $502_{1-M}$ in a second one-dimensional data vector, the data window $504_N$ can store an Nth portion of the sensor data $502_{1-M}$ in an Nth one-dimensional data vector, etc. In an embodiment, the data windows $504_{1-M}$ can concatenate a plurality of data channels associated with the sensor data $502_{1-M}$ into a single data channel.

Figure 6:
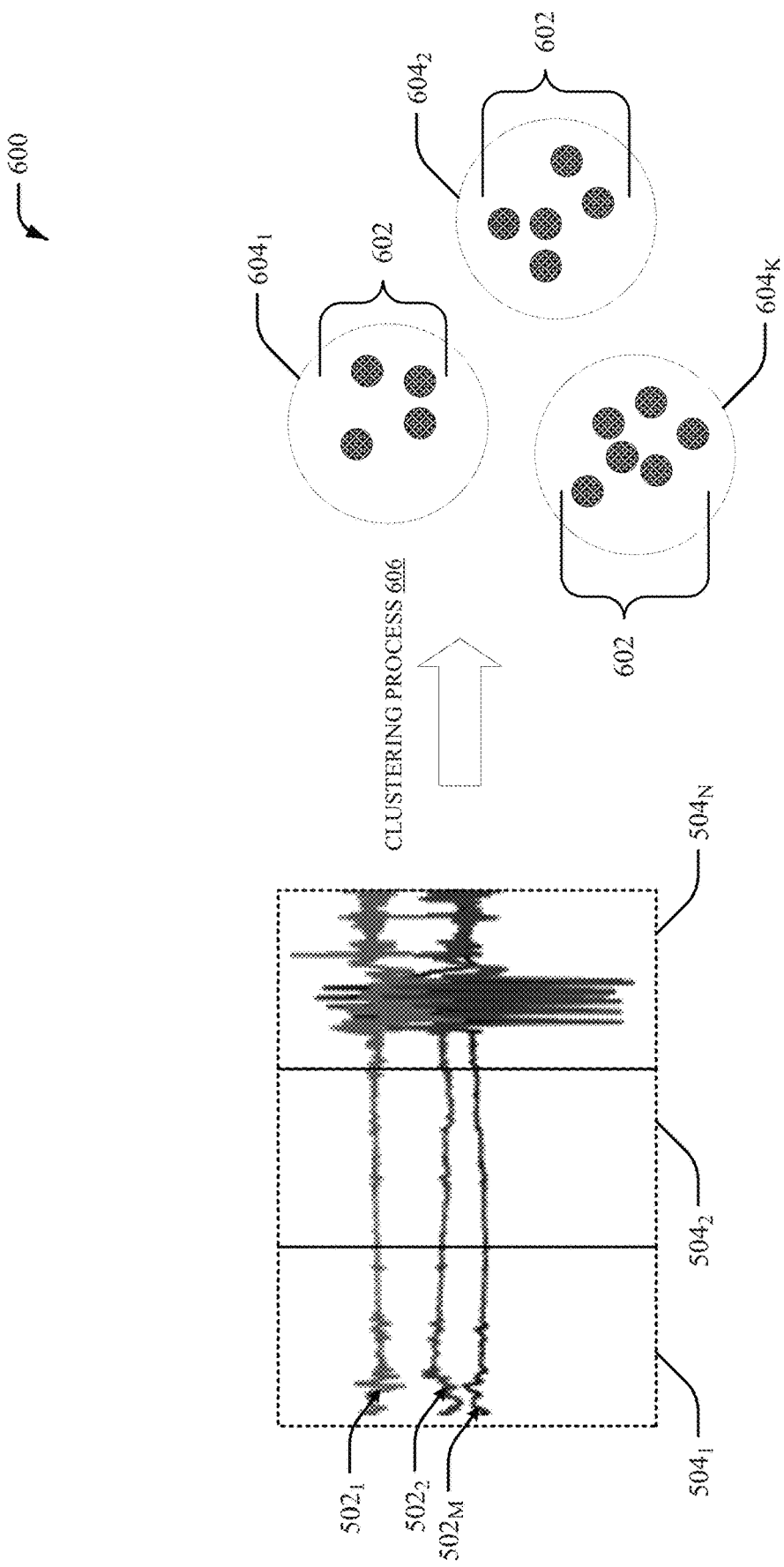
FIG. 6 illustrates an example, non-limiting system that includes a clustering process in accordance with one or more embodiments described herein.

FIG. 6 illustrates an example, non-limiting system 600 in accordance with one or more embodiments described herein. Repetitive description of like elements employed in other embodiments described herein is omitted for sake of brevity.

The system 600 includes the data windows $504_{1-M}$ associated with the sensor data $502_{1-M}$. In an aspect, a clustering process 606 can be performed to convert data 602 from the data windows $504_{1-M}$ into a set of data clusters $604_{1-K}$, where K is an integer. For instance, data 602 from the data windows $504_{1-M}$ associated with the sensor data $502_{1-M}$ can be partitioned into the set of data clusters $604_{1-K}$ (via the clustering process 606 where the set of data clusters $604_{1-K}$ (represent different groups and/or different classifications of the data 602. In an embodiment, the clustering process 606 can be a K-means clustering process. However, it is to be appreciated that the clustering process 606 can be a different type of clustering process to convert the data 602 from the data windows $504_{1-M}$ into the set of data clusters $604_{1-K}$.

Figure 7:
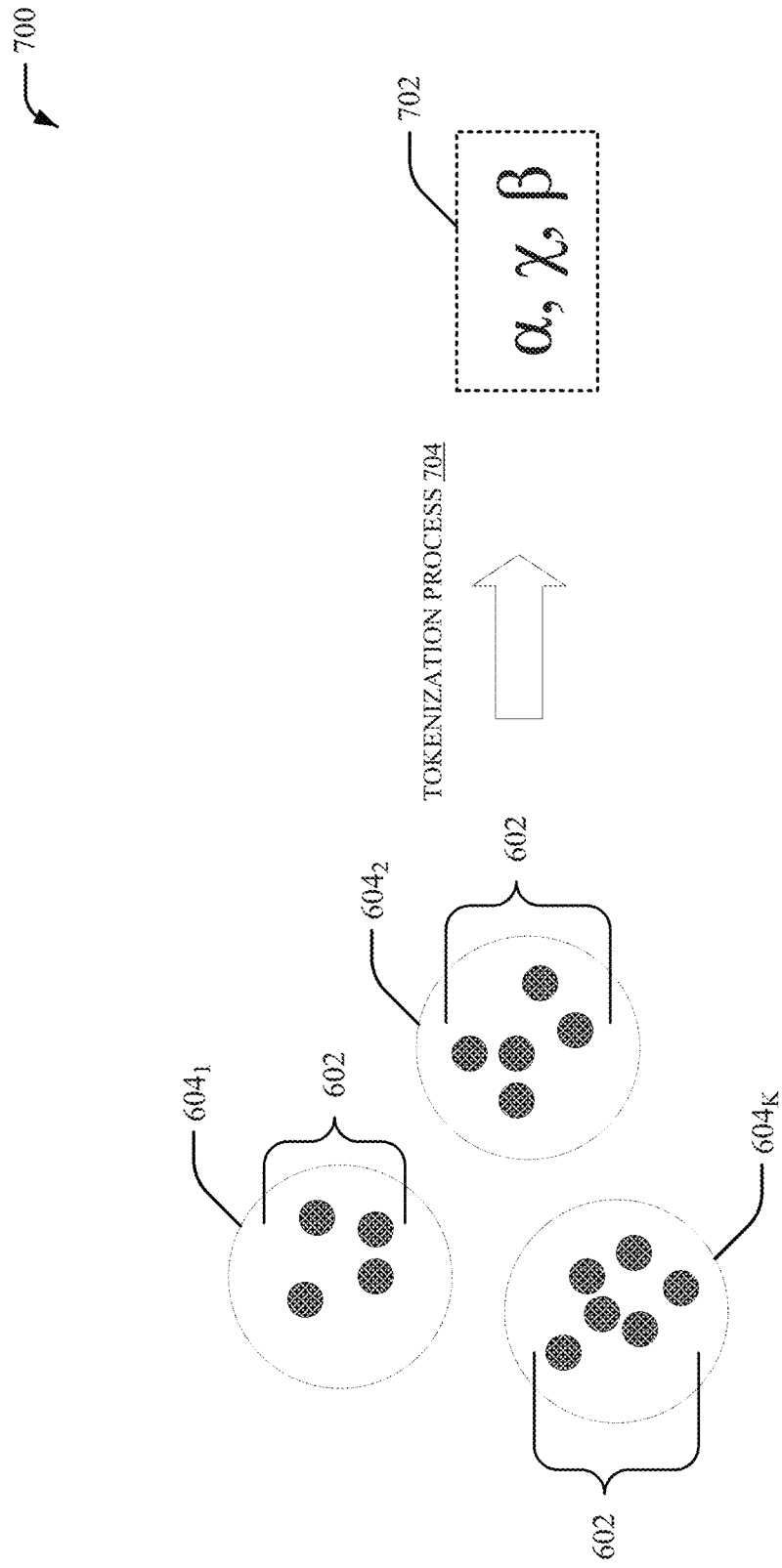
FIG. 7 illustrates an example, non-limiting system that includes a tokenization process in accordance with one or more embodiments described herein.

FIG. 7 illustrates an example, non-limiting system 700 in accordance with one or more embodiments described herein. Repetitive description of like elements employed in other embodiments described herein is omitted for sake of brevity.

The system 700 includes the set of data clusters $604_{1-K}$ (associated with the data 602. In an aspect, a tokenization process 704 can be performed to generate symbolic data 702 based on the set of data clusters $604_{1-K}$. For example, the data clusters $604_1$ can be represented by a first symbol (e.g., α) included in the symbolic data 702, the data clusters $604_2$ can be represented by a second symbol (e.g., χ) included in the symbolic data 702, the data clusters $604_K$ can be represented by a Kth symbol (e.g., β) included in the symbolic data 702, etc. The symbolic data can be associated with a natural language processing domain. As such, the data windows $504_{1-M}$ can be converted into a discrete symbolic representation via the tokenization process 704. For instance, the data windows $504_{1-M}$ can be tokenized into respective symbols (e.g., letters).

Figure 8:
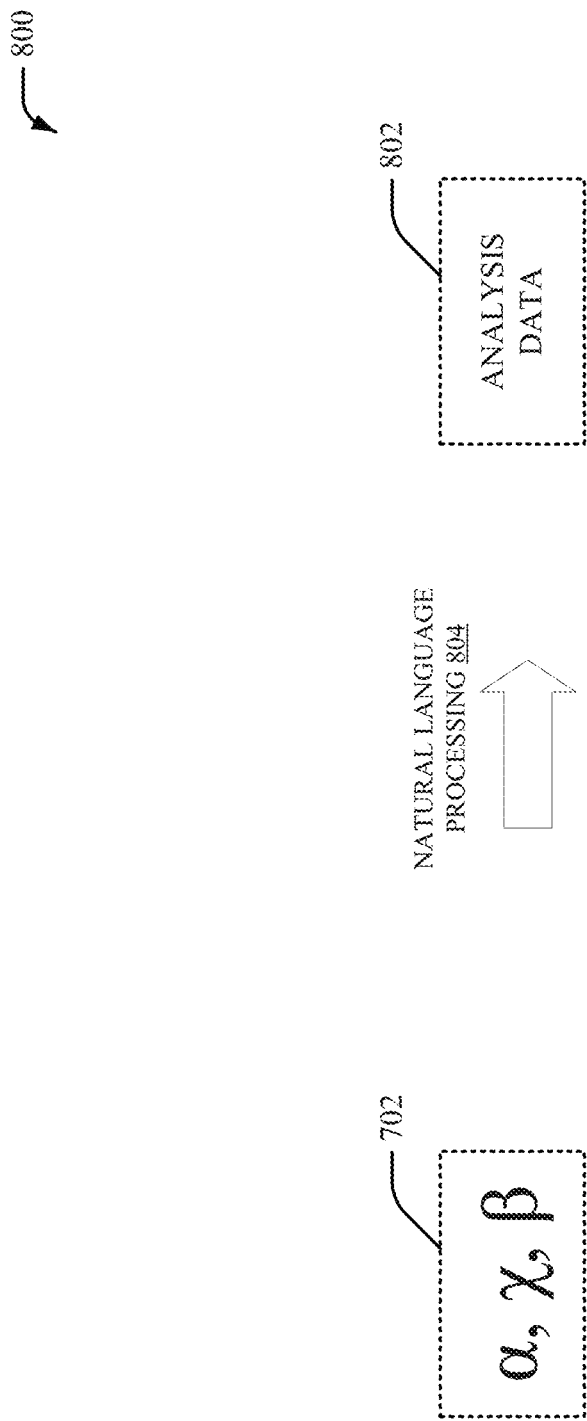
FIG. 8 illustrates an example, non-limiting system that includes a natural language processing in accordance with one or more embodiments described herein.

FIG. 8 illustrates an example, non-limiting system 800 in accordance with one or more embodiments described herein. Repetitive description of like elements employed in other embodiments described herein is omitted for sake of brevity.

The system 800 includes the symbolic data 702 and analysis data 802. In an embodiment, natural language processing 804 can analyze the symbolic data 702 to generate the analysis data 802. For instance, the symbolic data 702 can be modeled based on one or more natural language processing techniques associated with the natural language processing 804. For example, in an embodiment, the symbolic data 702 can be modeled based on a Markov-Chain technique associated with the natural language processing 804. However, it is to be appreciated that the natural language processing 804 can additionally or alternatively employ one or more other natural language processing techniques. In an aspect, the analysis data 802 can correspond to the analysis data 114 generated by the sensor analytics component 102. In one example, the analysis data 802 can include a natural language processing model. In certain embodiments, the analysis data 802 can include scoring data. The scoring data can be indicative of scoring information that indicates whether the sensor data $502_{1-M}$ is associated with a particular condition. For instance, the analysis data 802 can indicate a distance between derived distributions of the symbolic data 702 to a previously determined distribution of data. In one example, the analysis data 802 can provide motion behavior scoring for a user (e.g., a user identity) associated with the sensor data $502_{1-M}$. In another example, the analysis data 802 can indicate a whether the sensor data $502_{1-M}$ is associated with a medical condition (e.g., healthy vs. disease, etc.). In yet another example, the analysis data 802 can indicate a whether the sensor data $502_{1-M}$ is associated with a binary logic criterion (e.g., on vs. off, etc.).

Figure 9:
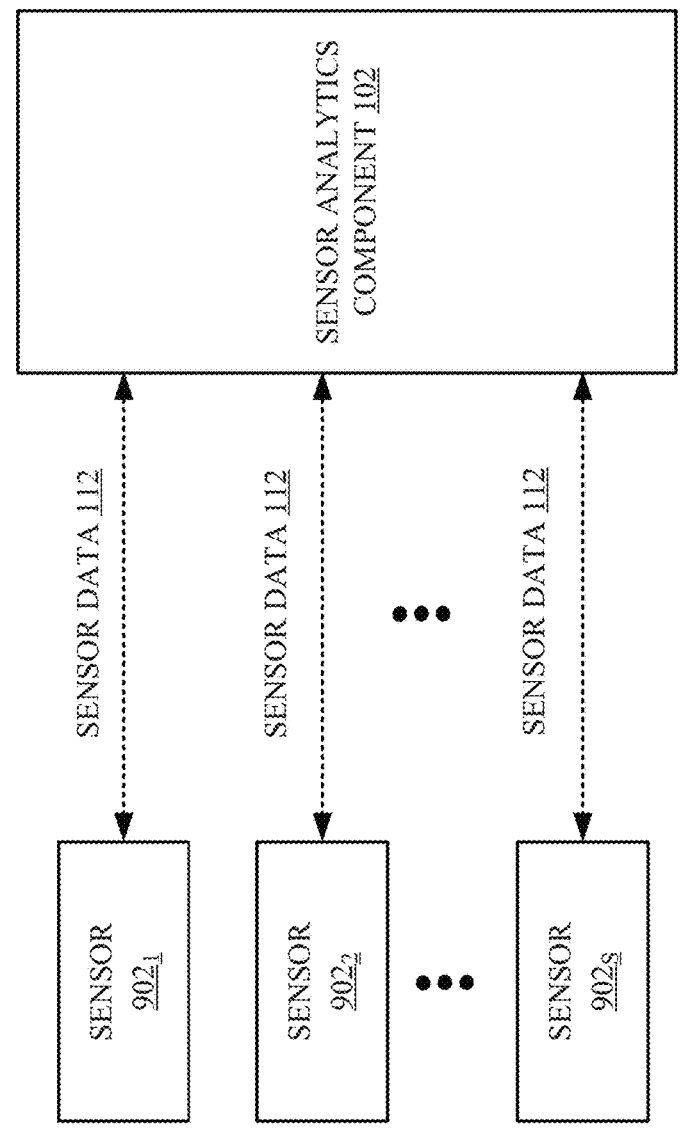
FIG. 9 illustrates an example, non-limiting system that includes one or more sensors and a sensor analytics component in accordance with one or more embodiments described herein.

FIG. 9 illustrates a block diagram of an example, non-limiting system 900 in accordance with one or more embodiments described herein. Repetitive description of like elements employed in other embodiments described herein is omitted for sake of brevity.

The system 900 includes one or more sensors $902_{1-S}$, wherein S is an integer. The system 900 also includes the sensor analytics component 102. In an aspect, the sensor analytics component 102 can receive the sensor data 112 from the one or more sensors $902_{1-S}$. For example, the sensor analytics component 102 can be in communication with the one or more sensors $902_{1-S}$ via a wireless network and/or a wired network associated with a wide area network (WAN, e.g., the Internet), a local area network (LAN), a cellular network, and/or communication network. In an aspect, the sensor analytics component 102 can repeatedly obtain the sensor data 112 from the one or more sensors $902_{1-S}$ during a period of time. The one or more sensors $902_{1-S}$ can be associated with a user (e.g., a user identity). For instance, the one or more sensors $902_{1-S}$ can be associated with a patient (e.g., a patient body). The one or more sensors $902_{1-S}$ can be one or more sensors of one or more sensor devices associated with the user (e.g., the user identity). For example, the one or more sensors $902_{1-S}$ can be one or more sensors of one or more movement capturing devices associated with the user (e.g., the user identity). Additionally or alternatively, the one or more sensors $902_{1-S}$ can be one or more sensors of one or more wearable devices associated with the user (e.g., the user identity). Additionally or alternatively, the one or more sensors $902_{1-S}$ can be one or more sensors of one or more medical wearable devices associated with the user (e.g., the user identity). Additionally or alternatively, the one or more sensors $902_{1-S}$ can be one or more sensors of one or more smart devices associated with the user (e.g., the user identity). However, it is to be appreciated that the one or more sensors $902_{1-S}$ can additionally or alternatively be one or more sensors of one or more different sensor devices associated with the user (e.g., the user identity). In an aspect, the one or more sensors $902_{1-S}$ can be worn by the user (e.g., the user identity). For example, the one or more sensors $902_{1-S}$ can be worn on the patient (e.g., worn on the patient body). In an embodiment, the one or more sensors $902_{1-S}$ can be one or more lumbar reference sensors. For example, the one or more sensors $902_{1-S}$ can be one or more accelerometers, one or more gyroscopes and/or one or more other movement capturing devices associated with a lumbar reference device. Additionally or alternatively, the one or more sensors $902_{1-S}$ can be one or more wearable sensors. For example, the one or more sensors $902_{1-S}$ can be one or more accelerometers, one or more gyroscopes, one or more magnetometers and/or one or more other movement capturing devices associated with a wearable device. In certain embodiments, the one or more sensors $902_{1-S}$ can additionally or alternatively be one or more biosensors that capture bio-activity associated with the user (e.g., the user identity). For example, the one or more sensors $902_{1-S}$ can be one or more electrocardiography sensors that obtain electrical activity of a biological heart of the patient during a certain time period. In certain embodiments, the one or more sensors $902_{1-S}$ can additionally or alternatively be one or more one or more auxiliary sensors located in one or objects and/or one or more devices auxiliary to the user (e.g., the user identity).

Figure 10:
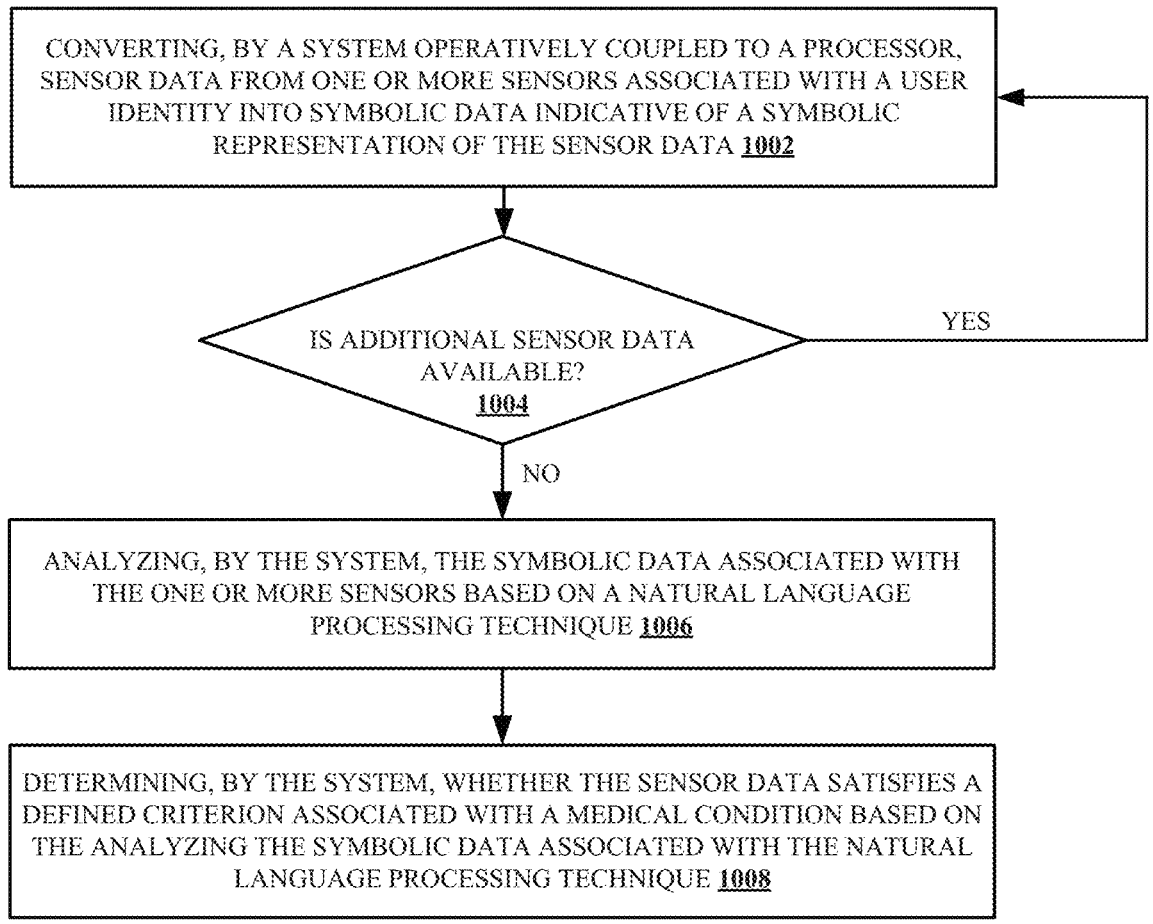
FIG. 10 illustrates a flow diagram of an example, non-limiting computer-implemented method for facilitating natural language processing of a motion alphabet for unsupervised clinical scoring in accordance with one or more embodiments described herein.

FIG. 10 illustrates a flow diagram of an example, non-limiting computer-implemented method 1000 for facilitating natural language processing of a motion alphabet for unsupervised clinical scoring in accordance with one or more embodiments described herein. At 1002, sensor data from one or more sensors associated with a user identity is converted, by a system operatively coupled to a processor (e.g., by measurement component 104), into symbolic data indicative of a symbolic representation of the sensor data. In one example, the sensor data can be associated with a patient (e.g., a patient body). The one or more sensors can be one or more sensors of one or more sensor devices associated with the user identity. For example, the one or more sensors can be one or more sensors of one or more movement capturing devices associated with the user identity. Additionally or alternatively, the one or more sensors can be one or more sensors of one or more wearable devices associated with the user identity. Additionally or alternatively, the one or more sensors can be one or more sensors of one or more medical wearable devices associated with the user identity. Additionally or alternatively, the one or more sensors can be one or more sensors of one or more smart devices associated with the user identity. However, it is to be appreciated that the one or more sensors can additionally or alternatively be one or more sensors of one or more different sensor devices associated with the user identity. In an aspect, the one or more sensors can be worn by a user associated with the user identity. For example, the one or more sensors can be worn on the patient (e.g., worn on the patient body). In an embodiment, the one or more sensors can be one or more wrist reference sensors. For example, the one or more sensors can be one or more accelerometers, one or more gyroscopes and/or one or more other movement capturing devices associated with a wrist reference device. Additionally or alternatively, the one or more sensors can be one or more lumbar reference sensors. For example, the one or more sensors can be one or more accelerometers, one or more gyroscopes and/or one or more other movement capturing devices associated with a lumbar reference device. Additionally or alternatively, the one or more sensors can be one or more wearable sensors. For example, the one or more sensors can be one or more accelerometers, one or more gyroscopes, one or more magnetometers and/or one or more other movement capturing devices associated with a wearable device. In certain embodiments, the one or more sensors can additionally or alternatively be one or more biosensors that capture bio-activity associated with the user identity. For example, the one or more sensors can be one or more electrocardiography sensors that obtain electrical activity of a biological heart of the patient during a certain time period. In certain embodiments, the one or more sensors can additionally or alternatively be one or more one or more auxiliary sensors located in one or objects and/or one or more devices auxiliary to the user identity.

The symbolic data can be representative of a motion alphabet related to the sensor data. In an aspect, the symbolic data can be a discrete representation of the sensor data that can be categorized into one or more classifications. For instance, the symbolic data can be a sequence of discrete symbols where a symbol is an identifier for a portion of the sensor data. In one example, the symbolic data can be a set of alphabetical letters associated with different portions of the sensor data. In another aspect, the symbolic data can be a compressed version of the sensor data. In an embodiment, a set of data windows associated with the sensor data can be captured to facilitate conversion of the sensor data into the symbolic data. For instance, the sensor data can be segmented into a set of data windows associated with a defined interval of time. In one example, the set of data windows can be a set of overlapping data windows. Furthermore, a set of symbols can be assigned to the set of data windows. For example, a first symbol can be assigned to a first data window from the set of data windows, a second symbol can be assigned to a second data window from the set of data windows, a third symbol can be assigned to a third data window from the set of data windows, etc. In an embodiment, the symbolic data can be stored in memory. In another embodiment, the symbolic data can be transmitted to a component and/or a server device. In certain embodiments, the sensor data can be converted into the symbolic data based on a clustering technique. For example, the sensor data can be converted into the symbolic data based on a K-means clustering technique.

At 1004, it is determined whether additional sensor data is available. If yes, the computer-implemented method 1000 returns to 1002. If no, the computer-implemented method 1000 proceed to 1006.

At 1006, the symbolic data associated with the one or more sensors is analyzed, by the system (e.g., by analysis component 106), based on a natural language processing technique. For example, syntax, semantics and/or discourse associated with the symbolic data can be determined using a natural language processing technique. The natural language processing technique can be an artificial intelligence technique that processes the symbolic data to learn and/or derive meaning from the symbolic data. In an aspect, the natural language processing technique can, for example, compute a characteristic distribution of the symbolic data that defines a probability distribution of the symbolic data. In another aspect, the natural language processing technique can generate a natural language processing model of the symbolic data. In an embodiment, the natural language processing technique can be a Markov-Chain technique. For instance, the Markov-Chain technique can generate a Markov chain for the symbolic data. The Markov chain can include a set of states associated with the symbolic data. Furthermore, the Markov chain can include a set of transitions between the set of states associated with the Markov chain. In an aspect, the Markov-Chain technique can, for example, compute a stationary distribution from the set of transitions associated with the Markov chain that defines a probability distribution of the symbolic data that can remain unchanged in the Markov chain during an interval of time. However, it is to be appreciated that the natural language processing technique can additionally or alternatively include one or more other natural language processing techniques.

At 1008, it is determined, by the system (e.g., by analysis component 106), whether the sensor data satisfies a defined criterion associated with a medical condition based on the analyzing the symbolic data associated with the natural language processing technique. For instance, data scoring of the sensor data can be performed based on the analysis of the symbolic data using the natural language processing technique. In one example, a feature vector that describes a state of the user identity (e.g., a patient motor state) can be determined based on the analysis of the symbolic data using the natural language processing technique. In certain embodiments, the analysis of the symbolic data using the natural language processing technique can provide improved processing and/or data scoring of the sensor data.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Moreover, because at least analyzing the symbolic data based on a natural language processing technique, etc. are established from a combination of electrical and mechanical components and circuitry, a human is unable to replicate or perform a condition detection process associated with the sensor analytics component 102 (e.g., the measurement component 104, the analysis component 106, the symbolic representation component 202, the filter component 302, and/or the natural language processing component 402) disclosed herein. For example, a human is unable to perform natural language processing, a human is unable to perform machine learning, a human is unable to generate symbolic data, a human is unable to generate analysis data, etc.

Figure 11:
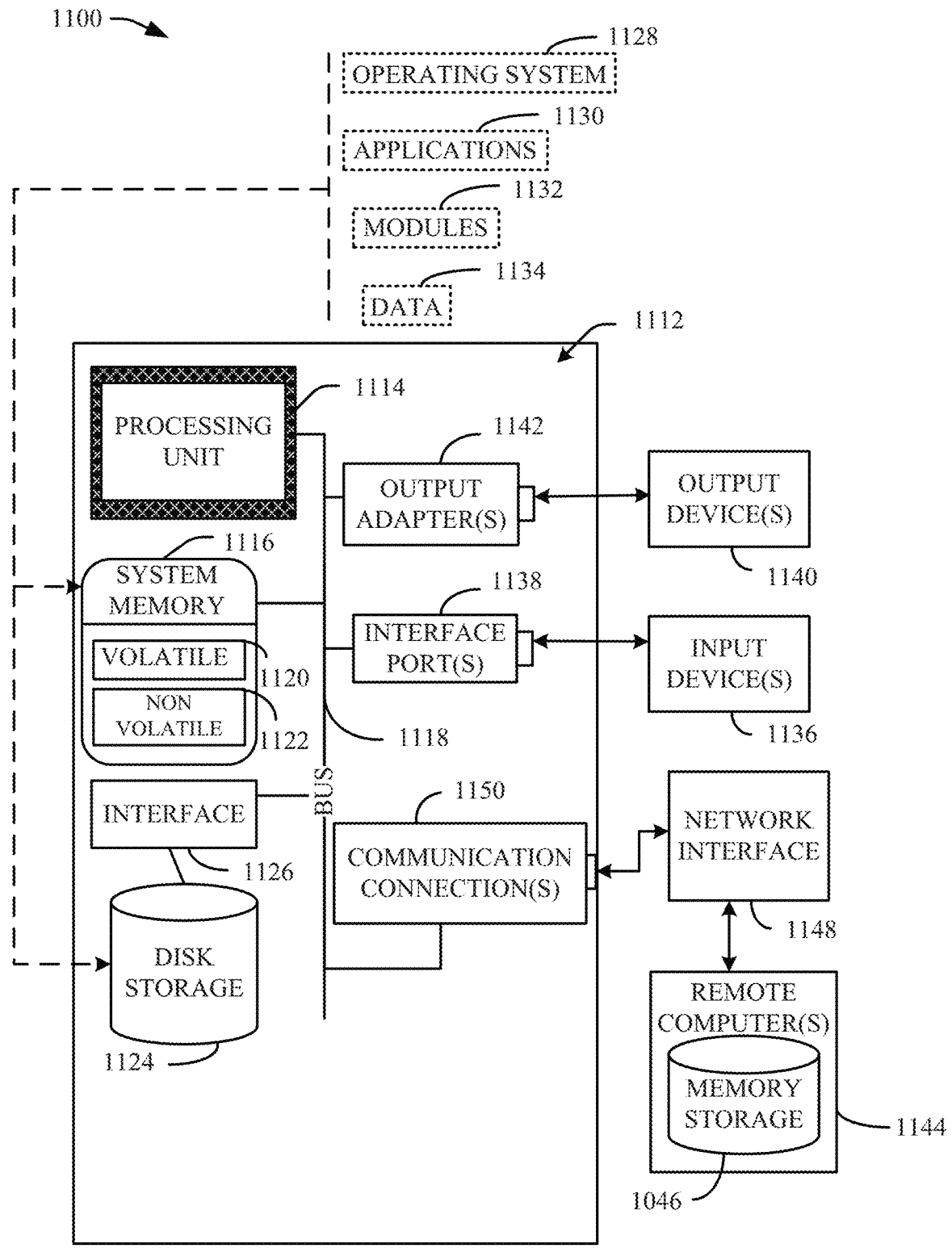
FIG. 11 illustrates a block diagram of an example, non-limiting operating environment in which one or more embodiments described herein can be facilitated.

In order to provide a context for the various aspects of the disclosed subject matter, FIG. 11 as well as the following discussion are intended to provide a general description of a suitable environment in which the various aspects of the disclosed subject matter can be implemented. FIG. 11 illustrates a block diagram of an example, non-limiting operating environment in which one or more embodiments described herein can be facilitated. Repetitive description of like elements employed in other embodiments described herein is omitted for sake of brevity.

With reference to FIG. 11, a suitable operating environment 1100 for implementing various aspects of this disclosure can also include a computer 1112. The computer 1112 can also include a processing unit 1114, a system memory 1116, and a system bus 1118. The system bus 1118 couples system components including, but not limited to, the system memory 1116 to the processing unit 1114. The processing unit 1114 can be any of various available processors. Dual microprocessors and other multiprocessor architectures also can be employed as the processing unit 1114. The system bus 1118 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1116 can also include volatile memory 1120 and nonvolatile memory 1122. The basic input/output system (BIOS), containing the basic routines to transfer information between elements within the computer 1112, such as during start-up, is stored in nonvolatile memory 1122. Computer 1112 can also include removable/non-removable, volatile/nonvolatile computer storage media. FIG. 11 illustrates, for example, a disk storage 1124. Disk storage 1124 can also include, but is not limited to, devices like a magnetic disk drive, floppy disk drive, tape drive, Jaz drive, Zip drive, LS-100 drive, flash memory card, or memory stick. The disk storage 1124 also can include storage media separately or in combination with other storage media. To facilitate connection of the disk storage 1124 to the system bus 1118, a removable or non-removable interface is typically used, such as interface 1126. FIG. 11 also depicts software that acts as an intermediary between users and the basic computer resources described in the suitable operating environment 1100. Such software can also include, for example, an operating system 1128. Operating system 1128, which can be stored on disk storage 1124, acts to control and allocate resources of the computer 1112.

System applications 1130 take advantage of the management of resources by operating system 1128 through program modules 1132 and program data 1134, e.g., stored either in system memory 1116 or on disk storage 1124. It is to be appreciated that this disclosure can be implemented with various operating systems or combinations of operating systems. A user enters commands or information into the computer 1112 through input device(s) 1136. Input devices 1136 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1114 through the system bus 1118 via interface port(s) 1138. Interface port(s) 1138 include, for example, a serial port, a parallel port, a game port, and a universal serial bus (USB). Output device(s) 1140 use some of the same type of ports as input device(s) 1136. Thus, for example, a USB port can be used to provide input to computer 1112, and to output information from computer 1112 to an output device 1140. Output adapter 1142 is provided to illustrate that there are some output devices 1140 like monitors, speakers, and printers, among other output devices 1140, which require special adapters. The output adapters 1142 include, by way of illustration and not limitation, video and sound cards that provide a means of connection between the output device 1140 and the system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. The remote computer(s) 1144 can be a computer, a server, a router, a network PC, a workstation, a microprocessor based appliance, a peer device or other common network node and the like, and typically can also include many or all of the elements described relative to computer 1112. For purposes of brevity, only a memory storage device 1146 is illustrated with remote computer(s) 1144. Remote computer(s) 1144 is logically connected to computer 1112 through a network interface 1148 and then physically connected via communication connection 1150. Network interface 1148 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1150 refers to the hardware/software employed to connect the network interface 1148 to the system bus 1118. While communication connection 1150 is shown for illustrative clarity inside computer 1112, it can also be external to computer 1112. The hardware/software for connection to the network interface 1148 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, Matlab, Python, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
 a memory that stores computer executable components;
 a processor that executes the computer executable components stored in the memory and that:
  stores, via data windows, sensor data from one or more movement capturing devices associated with a user identity as a set of vectors, wherein a first data window of the data windows stores a first portion of the sensor data as a first vector, and wherein a second data window of the data windows stores a second portion of the sensor data as a second vector;
  converts the sensor data into symbolic data indicative of a symbolic representation of the sensor data, wherein the sensor data is converted into symbolic data to facilitate compression of the sensor data for reduced storage and an improved data rate to transmit the sensor data;
  employs a Markov-Chain technique to compute a derived distribution associated with the symbolic data by generating a Markov chain that includes a set of states associated with the symbolic data and a set of transitions between the set of states, wherein the generating includes determining the set of transitions based on a changing distance between stationary distributions of sequences of the symbolic data, wherein each stationary distribution corresponds to an amount of time processing the symbolic data by the Markov-Chain technique and defines a probability distribution of the symbolic data that can remain unchanged in the Markov chain during an interval of time, and wherein the set of states comprise a healthy state and a diseased state;
  generates a natural language processing model that models the derived distribution along with a previously determined distribution;
  generates unsupervised scoring information associated with the symbolic data, wherein the unsupervised scoring information delineates a distance between the derived distribution of the symbolic data and the previously determined distribution within the natural language processing model; and
  labels the symbolic data as associated with a medical condition associated with the previously determined distribution or not associated with the medical condition associated with the previously determined distribution based on whether the unsupervised scoring information satisfies a defined criterion.

2. The system of claim 1, wherein the processor also assigns a first symbol of the symbolic data to the first data window and assigns a second symbol of the symbolic data to the second data window, wherein the first symbol is distinct from the second symbol and to generate a sequence of discrete symbols, and wherein the first data window and the second data window are overlapping, and wherein the processor also analyzes the symbolic data associated with the one or more movement capturing devices based on a natural language processing technique, and wherein the set of transitions between the set of states is determined based on a changing distance between derived distributions of symbol sequences associated with the symbolic data.

3. The system of claim 1, wherein the one or more movement capturing devices comprise a plurality of sensors that generate the sensor data, wherein a first type of the plurality of sensors is distinct from a second type of the plurality of sensors, wherein a first type comprises a biosensor that captures bioactivity from an entity associated with the user identity, wherein the plurality of sensors are auxiliary and remote from a body of the user identity, and wherein the medical condition is a neurological condition.

4. The system of claim 1, wherein the processor also converts the sensor data into the symbolic data based on a clustering technique that groups the sensor data employing a vector quantization of the sensor data.

5. The system of claim 1, wherein the processor further: classifies a medical condition and generates a confidence score related to the classification of the medical condition for the user identity.

6. The system of claim 1, wherein the processor also filters the sensor data based on filter data indicative of information for a range of movement associated with the user identity.

7. The system of claim 1, wherein the processor also receives the sensor data from one or more wearable devices, wherein the one or more movement capturing devices is one of the one or more wearable devices.

8. A computer-implemented method, comprising:
 storing, via data windows, by a system operatively coupled to a processor, sensor data from one or more sensors associated with a user identity as a set of vectors, wherein a first data window of the data windows stores a first portion of the sensor data as a first vector, and wherein a second data window of the data windows stores a second portion of the sensor data as a second vector;

converting, by the system, the sensor data into symbolic data indicative of a symbolic representation of the sensor data, wherein the sensor data is converted into symbolic data to facilitate compression of the sensor data for reduced storage and an improved data rate to transmit the sensor data;

employing, by the system, a Markov-Chain technique to compute a derived distribution associated with the symbolic data by generating a Markov chain that includes a set of states associated with the symbolic data and a set of transitions between the set of states, wherein the generating includes determining the set of transitions based on a changing distance between stationary distributions of sequences of the symbolic data, wherein each stationary distribution corresponds to an amount of time processing the symbolic data by the Markov-Chain technique and defines a probability distribution of the symbolic data that can remain unchanged in the Markov chain during an interval of time, and wherein the set of states comprise a healthy state and a diseased state;

generating, by the system, a natural language processing model that models the derived distribution along with a previously determined distribution;

generating, by the system, unsupervised scoring information associated with the symbolic data, wherein the unsupervised scoring information delineates a distance between the characteristic distribution of the symbolic data and the determined distribution within the natural language processing model; and labeling, by the system, the symbolic data as associated with a medical condition associated with the previously determined distribution or not associated with the medical condition associated with the previously determined distribution based on whether the unsupervised scoring information satisfies a defined criterion.

9. The method of claim 8, further comprising: receiving, by the system, the sensor data from one or more movement capturing devices associated with the sensor data, wherein the one or more sensors are located within the one or more movement capturing devices.

10. The method of claim 8, further comprising: receiving, by the system, the sensor data from one or more wearable devices associated with the sensor data, wherein the one or more sensors are located within one or more movement capturing devices.

11. The method of claim 8, wherein the converting comprises converting the sensor data into the symbolic data based on a clustering technique.

12. The method of claim 8, wherein the converting comprises capturing the data windows associated with the sensor data to facilitate the conversion of the sensor data into the symbolic data.

13. The method of claim 8, wherein the generating the natural language processing model comprises improving processing of the sensor data from the one or more sensors.

14. The method of claim 8, further comprising: classifying, by the system, a medical condition and generating a confidence score related to the classification of the medical condition for the user identity.

15. A non-transitory computer program product facilitating natural language processing of a motion alphabet for unsupervised clinical scoring, the computer program product comprising a computer readable storage medium having program instructions embodied therewith, the program instructions executable by a processor to cause the processor to:

store, via data windows and by the processor, sensor data from one or more sensors associated with a user identity as a set of vectors, wherein a first data window of the data windows stores a first portion of the sensor data as a first vector, and wherein a second data window of the data windows stores a second portion of the sensor data as a second vector;

convert, by the processor, the sensor data into symbolic data indicative of a symbolic representation of the sensor data, wherein the sensor data is converted into symbolic data to facilitate compression of the sensor data for reduced storage and an improved data rate to transmit the sensor data;

employ, by the processor, a Markov-Chain technique to compute a derived distribution associated with the symbolic data by generating a Markov chain that includes a set of states associated with the symbolic data and a set of transitions between the set of states, wherein the generating includes determining the set of transitions based on a changing distance between stationary distributions of sequences of the symbolic data, wherein each stationary distribution corresponds to an amount of time processing the symbolic data by the Markov-Chain technique and defines a probability distribution of the symbolic data that can remain unchanged in the Markov chain during an interval of time, and wherein the set of states comprise a healthy state and a diseased state;

generate, by the processor, a natural language processing model that models the derived distribution along with a previously determined distribution;

generate, by the processor, unsupervised scoring information associated with the symbolic data, wherein the unsupervised scoring information delineates a distance between the characteristic distribution of the symbolic data and the historic previously determined distribution within the natural language processing model; and label, by the processor, the symbolic data as associated with a medical condition associated with the previously determined distribution or not associated with the medical condition associated with the previously determined distribution based on whether the unsupervised scoring information satisfies a defined criterion.

16. The non-transitory computer program product of claim 15, wherein the program instructions are further executable by the processor to cause the processor to: receive, by the processor, sensor data from one or more wearable devices associated with the one or more sensors, wherein the one or more sensors are located within the one or more movement capturing devices.

* * * * *